US006730297B1

(12) United States Patent
Davidson et al.

(10) Patent No.: US 6,730,297 B1
(45) Date of Patent: May 4, 2004

(54) USE OF RECOMBINANT GENE DELIVERY VECTORS FOR TREATING OR PREVENTING LYSOSOMAL STORAGE DISORDERS

(75) Inventors: Beverly Davidson, North Liberty, IA (US); Douglas J. Jolly, Encinitas, CA (US); Sybille L. Sauter, Del Mar, CA (US); Colleen S. Stein, Iowa City, IA (US); Thomas W. Dubensky, Jr., Piedmont, CA (US); Jason A. Heth, Coralville, IA (US)

(73) Assignees: Chiron Corporation, Emeryville, CA (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/580,820

(22) Filed: May 26, 2000

Related U.S. Application Data

(60) Provisional application No. 60/136,527, filed on May 28, 1999.

(51) Int. Cl.[7] .......................... A01N 63/00; C12N 15/00; C12N 15/63; C12N 5/00
(52) U.S. Cl. .................. 424/93.21; 424/93.1; 424/93.2; 424/93.6; 435/320.1; 435/325; 435/455
(58) Field of Search .............................. 435/320.1, 325, 435/455; 424/93.1, 93.2, 93.21, 93.6

(56) References Cited

U.S. PATENT DOCUMENTS

| 5,089,392 A | 2/1992 | Miller et al. ................... 435/21 |
| 5,433,946 A | 7/1995 | Allen, Jr. et al. ........... 424/94.3 |

FOREIGN PATENT DOCUMENTS

| WO | WO 97/32983 | 9/1997 |
| WO | WO 98/41644 | 9/1998 |
| WO | 99/04026 | * 1/1999 |
| WO | WO 99/15641 | 4/1999 |
| WO | WO 99/36511 | 7/1999 |

OTHER PUBLICATIONS

Eck et al., Gene–Based Therapy, 1996, Goodman & Gilman's, Ninth Edition, pp. 77–101.*

Hartung et al., "Enzymatic Correction and Cross–Correction of Mucopolysaccharidosis Type 1 Fibroblasts by Adeno–Associated Virus–Mediated Transduction of the $\alpha$–$_L$–Iduronidase Gene," *Human Gene Therapy* 10:2163–2172 (1999).

Hughes et al., "Viral–Mediated Gene Transfer to Mouse Primary Neural Progenitor Cells," *Molecular Therapy* 5(1):16–24 (2002).

Takenaka et al., "Circulating $\alpha$–Galactosidase A Derived From Tansduced Bone Marrow Cells: Relevance for Corrective Gene Transfer for Fabry Disease," *Human Gene Therapy* 10:1931–1939 (1999).

Naffakh et al., "Gene Therapy for Lysosomal Disorders," *Nouv Rev Fr Hematol* 36(Suppl. 1):S11–S16 (1994).

Ali et al., "Adeno–Associated Virus Gene Transfer to Mouse Retina," *Human Gene Therapy* 9:81–86 (1998).

Ali et al., Gene Transfer into the Mouse Retina Mediated by an Adeno–Associated Viral Vector, *Human Mol. Genet* 5:591–594 (1996).

Bennett et al., "Real–Time, Noninvasive In Vivo Assessment of Adeno–Associated Virus–Mediated Retinal Transduction," *Invest Opthalmo Vis Sci* 38:2857–2863 (1997).

Borras et al., "Adenoviral Reporter Gene Transfer to the Human Trabecular Meshwork Does Not Alter Aqueous Humor Outlflow. Relevance for Potential Gene Therapy of Glaucoma," *Gene Therapy* 6:515–524 (1999).

Bosch et al., "Reversal of Pathology in the Entire Brain of Mucopolysaccharidosis Type VII Mice after Lentivirus–Mediated Gene Transfer," *Human Gene Therapy* 11:1139–1150 (2000).

Cone and Mulligan, "High Efficiency Gene Transfer into Mammalian Cells: Generation of Helper–Free Recombinant Retrovirus With Broad Mammalian Host Range," *Proc. Natl. Acad. Sci. U.S.A.* 814:6349 (1984).

Flannery et al., "Efficient Photoreceptor–Targeted Gene Expression In Vivo by Recombinant Adeno–Associated Virus," *Proc. Natl. Acad. Sci. U.S.A.* 94:6916–6921 (1997).

Jomary et al., "Rescue of Photoreceptor Function by AAV–Mediated Gene Transfer in a Mouse Model of Inherited Retinal Degeneration," *Gene Therapy* 4:683–690 (1997).

Li and Davidson, "Phenotype Correction in Retinal Pigment Epithelium in Murine Mucopolysaccharidosis VII by Adenovirus–Mediated Gene Transfer," *Proc. Natl. Acad. Sci. U.S.A.* 92:7700–7704(1995).

Li et al., "In Vivo Transfer of a Reporter Gene to the Retina Mediated by an Adenoviral Vector," *Inves Optahalmol Vis Sci* 35:2543–2549 (1994).

Mann et al., "Construction of a Retrovirus Packaging Mutant and Its Use to Produce Helper–Free Defective Retrovirus," *Cell* 33:153–159 (1983).

Miller et al., "Retrovirus Packaging Cells," *Human Gene Therapy* 1:5–14 (1990).

Miyoshi et al., "Stable and Efficient Gene Transfer into the Retina Using an HIV–Based Lentiviral Vector,"*Proc. Natl. Acad. Sci. U.S.A.* 94:10319–10323 (1997).

Miyoshi et al., "Development of a Self–Inactivating Lentivirus Vector," *Journal of Virology* 72(10):8150–8157 (1998).

Ohashi et al., "Adenovirus–Mediated Gene Transfer and Expression of Human $\beta$–Glucuronidase Gene in the Liver, Spleen, and Central Nervous System in Mucopolysaccharidosis Type VII Mice," *Proc. Natl. Acad. Sci. USA* 94:1287–1292 (1997).

(List continued on next page.)

*Primary Examiner*—Shin-Lin Chen
(74) *Attorney, Agent, or Firm*—Roberta L. Robins; Alisa A. Harbin; Robert P. Blackburn

(57) ABSTRACT

Gene delivery vectors, for example, recombinant FIV vectors, and methods of using such vectors are provided for use in treating or preventing retinal diseases of the eye and diseases of the brain associated with lysosomal storage disorders.

13 Claims, 5 Drawing Sheets

OTHER PUBLICATIONS

Rolling et al., "Evaluation of Adeno–Associated Virus–Mediated Gene Transfer into the Rat Retina by Clinical Fluorescence Photography," *Human Gene Ther* 10:641–648 (1999).

Sakamoto et al., "Target Gene Transfer of Tissue Plasminogen Activator to Cornea by Electric Pulse Inhibits Intracameral Fibrin Formation and Corneal Cloudiness," *Human Gene Therapy* 5:1088–1097 (1999).

Sands et al., "Gene Therapy for Murine Mucopolysaccharidosis Type VII," *Neuromuscular Disorders* 7:352–360 (1997).

Takahashi et al., "Rescue from Photoreceptor Degeneration in the rd Mouse by Human Immunodeficiency Virus Vector–Mediated Gene Transfer," *Journal of Virology* 73:7812–7816 (1999).

Volgler et al., "Murine Mucopolysaccharidosis Type VII: The Impact of Therapies on the Clinical Course and Pathology in a Murine Model of Lysosomal Storage Disease," *J. Inher. Metab. Dis.* 21:575–586 (1998).

Watson et al., "Treatment of Lysosomal Storage Disease in MPS VII Mice using a Recombinant Adeno–Associated Virus," *Gene Therapy* 5:1642–1649 (1998).

\* cited by examiner

Control     Contralateral Cortex     Contralateral Striatum

USE OF RECOMBINANT GENE DELIVERY VECTORS FOR TREATING OR PREVENTING LYSOSOMAL STORAGE DISORDERS

CROSS-REFERENCE TO RELATED APPLICATION

This application is related to provisional patent application Ser. No. 60/136,527, filed May 28, 1999, from which priority is claimed under 35 USC §119(e)(1) and which is incorporated herein by reference in its entirety.

This invention was made with support under NIH Grants NS34568, DK5479, MH57047 and HD33531 from the National Institutes of Health, U.S. Department of Health and Human Services. Accordingly, the United States Government may have certain rights in this invention.

TECHNICAL FIELD

The present invention relates to compositions and methods for treating diseases of the eye, and more specifically, to the use of various gene delivery vectors which direct the expression of selected gene products suitable for treating or preventing diseases of the eye and brain associated with lysosomal storage disorders and other genetic defects.

BACKGROUND OF THE INVENTION

Mucopolysaccharidoses (MPS) refer to a group of inherited lysosomal storage diseases, each of which is caused by the deficiency of a lysosomal enzyme that degrades glycosaminoglycans (GAGs). MPS patients exhibit undegraded GAGs in lysosomes, leading to lysosomal distention and progressive cellular and organ dysfunction, caused by accumulation of chondroitin, dermatan and heparan sulphate. Patients afflicted with MPS can have a variety of clinical features including short stature, progressive bone and joint abnormalities termed dysostosis multiplex, course facial features, deafness, corneal clouding, hepatosplenomegaly, mental retardation and premature death. The lysosomal storage defect can occur in the viscera, brain and skeleton, and the accumulated GAGs have a fibrillogranular appearance ultrastructurally (Vogler et al., *J. Inher. Metab. Dis.* 21:575–586, 1998).

One member of this disease group is a hereditary retinal disease caused by β-glucuronidase deficiency. Also known as MPS VII, it is a progressive condition, with most tissues affected including the CNS.

Canine and murine models of MPS VII have been described (Haskins et al., *Pediatr Res* 18:980–984, 1984; Birkenmeier et al., *J Clin Invest* 83:1258–1256, 1989). The MPS mouse shares many common features with human patients, including the ocular pathology (Li and Davidson, *PNAS* 92:7700–7704, 1995; Volger et al., *Am J Pathol* 136:207–217, 1990). These shared features make the MPS mouse an attractive model for studying experimental treatment of a lysosomal disease. For example, cells in diseased tissues contain numerous distended lysosomes. In the brain, both neurons and cells of glial lineage are affected. In the eye, the retinal pigment epithelium (RPE) is affected.

Gene therapy has been used to treat a variety of disorders and gene transfer to the eye has been attempted using recombinant vectors such as adenovirus (Li et al., *Invest Opthalmol Vis Sci* 35:2543–2549, 1994; Borras et al., *Gene Ther* 6:515–524, 1999; Li and Davidson, *PNAS* 92:7700–7704, 1995; Sakamoto et al., *H Gene Ther* 5:1088–1097, 1999) adeno-associated virus (Ali et al., *Hum Gene Ther* 9:81–86, 1998, Flannery et al., *PNAS* 94:6916–6921, 1997; Bennett et al., *Invest Opthalmol Vis Sci* 38:2857–2863, 1997; Jomary et al., Gene Ther 4:683–690, 1997, Rolling et al., *Hum Gene Ther* 10:641–648, 1999; Ali et al., *Hum Mol Genet* 5:591–594, 1996) and human immunodeficiency virus (Miyoshi et al., *PNAS* 94:10319–23, 1997; Takahashi et al., *J Virol* 73:7812–7816, 1999). Each of these viruses infect slightly different populations of cells. For example, an intravitreal injection of adenovirus infects cells only in the anterior segment of the eye, mainly the corneal endothelium and iris pigmented epithelium, while a subretinal injection results mainly in positive RPE and muller cells (Li et al., *Invest Opthalmol Vis Sci* 35:2543–2549, 1994; Li and Davidson, *PNAS* 92:7700–7704, 1995; Sakamoto et al., *H Gene Ther* 5:1088–1097, 1999. AAV injected intravitreally results in transduction of the ganglion cell layer and the RPE. A subretinal injection produces positive photoreceptors, in addition to the RPE and ganglion cells (Ali et al., *Hum Mol Genet* 5:591–594, 1996). Studies with HIV injected subretinally have shown efficient transduction of the RPE and photoreceptors (Miyoshi et al., *PNAS* 94:10319–23, 1997; Takahashi et al., *J Virol* 73:7812–7816, 1999).

Recombinant retroviral gene delivery methods have been extensively utilized in other gene therapy approaches, in part due to: (1) the efficient entry of genetic material (the vector genome) into cells; (2) an active, efficient process of entry into the target cell nucleus; (3) relatively high levels of gene expression; (4) the potential to target particular cellular subtypes through control of the vector-target cell binding and the tissue-specific control of gene expression; (5) a general lack of pre-existing host immunity; (6) substantial knowledge and clinical experience which has been gained with such vectors; and (7) the capacity for stable and long-term expression.

Briefly, retroviruses are diploid positive-strand RNA viruses that replicate through an integrated DNA intermediate. Upon infection by the RNA virus, the retroviral genome is reverse-transcribed into DNA by a virally encoded reverse transcriptase that is carried as a protein in each retrovirus. The viral DNA is then integrated pseudorandomly into the host cell genome of the infected cell, forming a "provirus" which is inherited by daughter cells.

One type of retrovirus, the murine leukemia virus, or "MLV", has been widely utilized for gene therapy applications (see generally Mann et al. *Cell* 33:153, 1983; Cane and Mulligan, *PNAS* 81:6349, 1984; and Miller et al., *Human Gene Therapy* 1:5–14, 1990). One major disadvantage of MLV-based vectors, however, is that the host range (i.e., cells infected with the vector) is limited, and the frequency of transduction of non-replicating cells is generally low.

Feline immunodeficiency virus ("FIV")-mediated gene therapy vector systems have also been described (see, International Publication Nos. WO 99/15641 and WO 99/36511).

The present invention provides compositions and methods for treating and preventing a number of retinal and brain diseases and degenerations such as RP and AMD, using retrovirus-mediated gene transfer and, further, provides other related advantages.

SUMMARY OF THE INVENTION

The present invention provides compositions and methods for treating, preventing, or inhibiting diseases of the eye and the brain, and in particular, diseases of the eye and brain that result from iysosomal storage disease or from deficiency of retinal gene products. Within one aspect of the present invention, methods are provided for treating or preventing diseases of the eye or brain comprising the step of intravitreal administration of a gene delivery vector which directs the expression of one or more polypeptides, proteins or enzymes, such that the disease is treated or prevented. Within certain embodiments of the invention, a viral promoter (e.g., CMV), a tissue-specific promoter (e.g., opsin or RPE), or an inducible promoter (e.g., tet) is utilized to drive the expression of the polypeptide, protein or enzyme factor.

Preferred gene delivery vectors suitable for use within the present invention may be generated from retroviruses such as FIV or HIV.

Utilizing the methods and gene delivery vectors provided herein a wide variety of retinal diseases may be readily treated or prevented, including for example, macular degeneration, diabetic retinopathies, inherited retinal degeneration such as retinitis pigmentosa, glaucoma, retinal detachment or injury and retinopathies. Genes encoding a wide variety of polypeptides, proteins or enzymes may be employed, including those which, when expressed, prevent or alleviate the effects of the lysosomal storage disorder. An example is β-glucuronidase.

The invention therefore relates to a method of treating or preventing retinal diseases of the eye, comprising, administering intravitreously a gene delivery vector which directs the expression of a polypeptide, protein or enzyme, such that said retinal disease of the eye is treated or prevented.

In certain embodiments, the protein, polypeptide or enzyme is selected from the group consisting of β-glucuronidase; neuraminidase; sphingomyelinase; sulfatases; arylsulfatase β; β-galactosidase; α-galactosidase; ceramidase; glucocerebrosidase; β-hexosaminidase; galactosylceramidase; arylsulfatase A; α-N-acetylgalactosaminidase; aspartylglycosaminidase; α-L-fucosidase; α-mannosidase; β-mannosidase; sialidase; iduronate sulfatase; α-L-iduronidase; GalNac-4-sulfatase; Gal 6-sulfatase; heparin N-sulfatase; α-N-acetylglucosaminidase; acetyl-CoA; GlnNAc 6-sulfatase; α-glucosidase; acid lipase; 6-phospho-N-acetylglycosamine transferase; α-neuraminidase; gangliosidase; tripeptidyl protease; CLN3; and palmitoyl protein thioesterase (PPT).

The invention further relates to treating retinal disease of the eye such as macular degeneration; diabetic retinopathy, inherited retinal degeneration, such as retinitis pigmentosa; and glaucoma.

According to the invention, the said gene delivery vector is a retrovirus selected from the group consisting of HIV and FIV.

The invention further provides methods of treating diseases including Sly syndrome; Salla disease; infantile sialic acid storage disease; cystinosis; Morbus Gaucher disease; type 1 sialidosis; Batten's disease; Mucolipidosis Type IV; Hermansky-Pudlak syndrome; gangliosidosis; galactosialidosis; Type B Niemann-Pick disease; multiple sulfatase deficiency; Austin's disease; Morquio syndrome; arylsulfatase B deficiency; neuraminidase deficiency; β-galactosidase deficiency; Hurler's disease; Hunter's disease; Fabry disease; Farber disease; metachromatic leukodystropy; Niemann-Pick disease; Schindler disease; aspartylglycosaminuria; fucosidosis; α-mannosidosis; β-mannosidosis; sialidosis; Maroteaux-Lamy syndrome; Sanfilippo syndrome; Pompe disease (glycogenosis II); Wolman disease; I-cell disease; pseudo Hurler polydystrophy; and Krabbe disease.

According to a preferred embodiment, the invention provides a method of treating or preventing cell damage in retinal epithelial cells associated with Sly syndrome in a human comprising administering to the human a gene delivery vector that directs the expression of β-glucuronidase.

In a particularly preferred embodiment, the gene delivery vector is FIV.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIGS. 2A and 2 B show a comparison of brain sections from a normal (2A) and MPS VII-affected (2B) mouse.

DETAILED DESCRIPTION OF THE INVENTION

Figure 1:
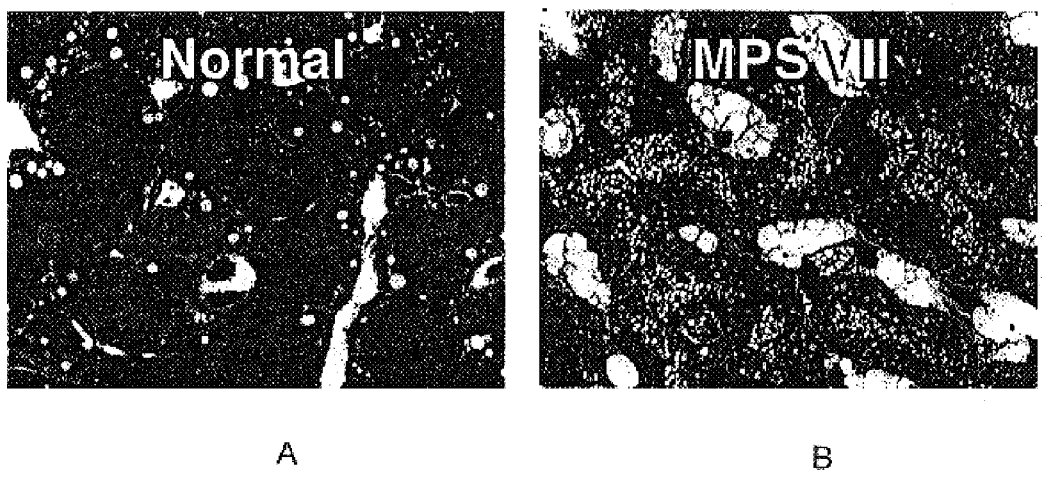
FIGS. 1A and 1B show a comparison of liver sections from a normal (1A) and MPS VII-affected (1B) mouse.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2 nd Edition, 1989); *Methods In Enzymology* (S. Colowick and N. Kaplan eds., Academic Press, Inc.); *Remington's Pharmaceutical Sciences*, 18 th Edition (Easton, Pa.: Mack Publishing Company, 1990).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

Definitions

In describing the present invention, the following terms will be employed, and are intended to be defined as indicated below.

"Gene delivery vehicle" refers to a construct which is capable of delivering, and, within preferred embodiments expressing, one or more gene(s) or sequence(s) of interest in a host cell. Representative examples of such vehicles include viral vectors, nucleic acid expression vectors, naked DNA, and certain eukaryotic cells (e.g., producer cells).

The terms "lentiviral vector construct," "lentiviral vector," and "recombinant lentiviral vector" are used interchangeably herein and refer to a nucleic acid construct derived from a lentivirus which carries, and within certain embodiments, is capable of directing the expression of a nucleic acid molecule of interest. Lentiviral vectors can have one or more of the lentiviral wild-type genes deleted in whole or part, as described further below, but retain functional flanking long-terminal repeat (LTR) sequences (also described below). Functional LTR sequences are necessary for the rescue, replication and packaging of the lentiviral virion. Thus, a lentiviral vector is defined herein to include at least those sequences required in cis for replication and packaging (e.g., functional LTRs) of the virus. The LTRs need not be the wild-type nucleotide sequences, and may be altered, e.g., by the insertion, deletion or substitution of nucleotides, so long as the sequences provide for functional rescue, replication and packaging.

Generally, a lentiviral vector includes at least one transcriptional promoter or promoter/enhancer or locus defining element(s), or other elements that control gene expression by other means such as alternate splicing, RNA export, post-translational modification of messenger, or post-transcriptional modification of protein. As explained above, such vector constructs also include a packaging signal, LTRs or functional portions thereof, and positive and negative strand primer binding sites appropriate to the retrovirus used (if these are not already present in the retroviral vector). Optionally, the recombinant lentiviral vector may also include a signal that directs polyadenylation, selectable and/or non-selectable markers, an origin of second strand DNA synthesis, as well as one or more restriction sites and a translation termination sequence. Examples of markers include, but are not limited to, neomycin (Neo), thymidine kinase (TK), hygromycin, phleomycin, puromycin, histidinol, green fluorescent protein (GFP), human placental alkaline phosphatase (PLAP), DHFR, β-galactosidase and human growth hormone (hGH). By way of example, such vectors typically include a 5' LTR, a tRNA binding site, a packaging signal, an origin of second strand DNA synthesis, and a 3' LTR or a portion thereof.

The terms "FIV retroviral vector construct," "FIV vector," and "recombinant FIV vector" are used interchangeably to refer to a lentiviral vector construct, as defined above, which includes one or more FIV sequences. By way of example, such vectors typically include a 5' FIV LTR, a primer binding site, a packaging signal, an origin of second strand DNA synthesis, and a 3' FIV LTR. Heterologous sequences that are included in the vector construct are those which encode a protein, such as an enzyme, the expression of which is deficient in the selected target cells.

"Expression cassette" refers to an assembly which is capable of directing the expression of the sequence(s) or gene(s) of interest. The expression cassette includes a promoter or promoter/enhancer which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Packaging cell" refers to a cell which contains those elements necessary for production of infectious recombinant retrovirus which are lacking in a recombinant retroviral vector. Packaging cells contain one or more expression cassettes which are capable of expressing proteins which encode gag, pol and env-derived proteins. Packaging cells can also contain expression cassettes encoding one or more of vif rev, or ORF 2 in addition to gag/pol and env expression cassettes.

"Producer cell" and "Vector Producing Cell Line" (VCL) refer to a cell which contains all elements necessary for production of recombinant vector particles.

"Lentiviral vector particle" as used herein refers to a recombinant lentivirus which carries at least one gene or nucleotide sequence of interest, which is generally flanked by lentiviral LTRs. The lentivirus may also contain a selectable marker. The recombinant lentivirus is capable of reverse transcribing its genetic material into DNA and incorporating this genetic material into a host cell's DNA upon infection. Lentiviral vector particles may have a lentiviral envelope, a non-lentiviral envelope (e.g., an amphotropic or VSV-G envelope), a chimeric envelope or a modified envelope (e.g., truncated envelopes or envelopes containing hybrid sequences).

"FIV vector particle" as utilized herein refers to a lentiviral particle, as defined above, which is derived from FIV.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. Gene 13:197, 1981. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant lentiviral vector particle.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5," or "3" relative to another sequence, it is to be understood that it is the position of the sequences in the non-transcribed strand of a DNA molecule that is being referred to as is conventional in the art.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By "vertebrate subject" is meant any member of the subphylum chordata, including, without limitation, mammals such as cattle, sheep, pigs, goats, horses, and human and non-human primates; domestic animals such as dogs and cats; laboratory animals including rodents such as mice, rats and guinea pigs, and the like; birds, including domestic, wild and game birds such as cocks and hens including chickens, turkeys and other gallinaceous birds; and fish. The term does not denote a particular age. Thus, both adult and newborn animals, as well as fetuses, are intended to be covered.

Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention provides compositions and methods for treating, preventing, or, inhibiting retinal diseases of the eye, comprising the general step of administering intravitreously a recombinant FIV vector which directs the expression of one or more polypeptides, proteins or enzymes, such that the retinal disease of the eye is treated or prevented. The invention also provides compositions and methods for treating, preventing, or inhibiting diseases of the brain related to lysosomal storage disorders. In order to further an understanding of the invention, a more detailed discussion is provided below regarding (A) gene delivery vectors; (B) polypeptides, proteins or enzymes for use in treating lysosomal storage diseases; and (C) methods of administering the gene delivery vectors in the treatment or prevention of retinal diseases of the eye and diseases of the brain.

A. Gene Delivery Vectors

1. Construction of Retroviral Gene Delivery Vectors

Within one aspect of the present invention, retroviral gene delivery vehicles are provided which are constructed to carry or express a selected gene(s) or sequence(s) of interest. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110–2209), or isolated from known sources using commonly available techniques.

Any of the above retroviruses may be readily utilized in order to assemble or construct retroviral gene delivery vehicles given the disclosure provided herein, and standard recombinant techniques (e.g., Sambrook et al, *Molecular Cloning: A Laboratory Manual*, 2 d ed., Cold Spring Harbor Laboratory Press, 1989; Kunkle, *PNAS* 82:488, 1985). In addition, within certain embodiments of the invention, portions of the retroviral gene delivery vehicles may be derived from different retroviruses. For example, within one embodiment of the invention, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Within one aspect of the present invention, retrovector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences.

Within certain embodiments of the invention, retrovirus vectors are provided wherein viral promoters, preferably CMV or SV40 promoters and/or enhancers are utilized to drive expression of one or more genes of interest.

Within other aspects of the invention, retrovirus vectors are provided wherein tissue-specific promoters are utilized to drive expression of one or more genes of interest.

Retrovirus vector constructs for use with the subject invention may be generated such that more than one gene of interest is expressed. This may be accomplished through the use of di- or oligo-cistronic cassettes (e.g., where the coding regions are separated by 120 nucleotides or less, see generally Levin et al., *Gene* 108:167–174, 1991), or through the use of Internal Ribosome Entry Sites ("IRES").

Within one aspect of the invention, self-inactivating (SIN) vectors are made by deleting promoter and enhancer elements in the U3 region of the 3'LTR, including the TATA box and binding sites for one or more transcription factors. The deletion is transferred to the 5'LTR after reverse transcription and integration in transduced cells. This results in the transcriptional inactivation of the LTR in the provirus. Possible advantages of SIN vectors include increased safety of the gene delivery system as well as the potential to reduce promoter interference between the LTR and the internal promoter which may result in increased expression of the gene of interest. Furthermore, it is reasonable to expect tighter control of regulatable gene therapy vectors due to the lack of an upstream promoter element in the 5'LTR.

FIV vectors are particularly preferred for use herein. FIV vectors may be readily constructed from a wide variety of FIV strains. Representative examples of FIV strains and molecular clones of such isolates include the Petaluma strain and its molecular clones FIV34TF10 and FIV14 (Olmsted et al., *PNAS* 86:8088–8092, 1989; Olmsted et al., *PNAS* 86:2448–2452, 1989; Talbot et al., *PNAS* 86:5743–5747, 1989), the San Diego strain and its molecular clone PPR (Phillips et al., *J Virology* 64:4605–4613, 1990), the Japanese strains and their molecular clones FTM191CG and FIV-TM2 (Miyazawa et al., *J. Virology* 65:1572–1577, 1991) and the Amsterdam strain and its molecular clone 19K1 (Siebelink et al., *J. Virology* 66:1091–1097, 1992). Such FIV strains may either be obtained from feline isolates, or more preferably, from depositories or collections such as the ATCC, or isolated from known sources using commonly available techniques.

Any of the above FIV strains may be readily utilized in order to assemble or construct FIV gene delivery vehicles given the disclosure provided herein, and standard recombinant techniques (e.g., Sambrook et al., *Molecular Cloning: A laboratory Manual*, 2 nd ed., Cold Spring Harbor Laboratory Press, 1989; Kunkle, *PNAS* 82:488, 1985; International Publication Nos. WO 99/15641 and WO 99/36511). In addition, within certain embodiments of the invention, portions of the FIV gene delivery vehicles may be derived from different viruses. For example, within one embodiment of the invention, recombinant FIV vector or LTR sequences may be partially derived or obtained from HIV, a packaging signal from SIV, and an origin of second strand synthesis from HIV-2.

Within one aspect of the present invention, FIV vector constructs are provided comprising a 5' FIV LTR, a tRNA binding site, a packaging signal, one or more heterologous sequences, an origin of second strand DNA synthesis, an RNA export element and a 3' FIV LTR. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. For purposes of the present invention, a 5' FIV LTR should be understood to include as much of the native 5' FIV LTR in order to function as a 5' promoter or promoter/enhancer element to allow reverse transcription and integration of the DNA form of the vector. The 3' FIV LTR should be understood to include as much of the 3' FIV LTR to function as a polyadenylation signal to allow reverse transcription and integration of the DNA form of the vector.

Additionally, FIV vector constructs may contain hybrid FIV LTRs where up to 75% of the wildtype FIV LTR sequence is deleted and replaced by one or more viral or non-viral promoter or promoter/enhancer elements (e.g., other retroviral LTRs and/or non-retroviral promoters or promoter/enhancers such as the CMV promoter/enhancer or the SV40 promoter) similar to the hybrid LTRs described by Chang, et al., *J. Virology* 67, 743–752, 1993; Finer, et al., *Blood* 83, 43–50, 1994 and Robinson, et al., *Gene Therapy* 2, 269–278, 1995.

The tRNA binding site and origin of second strand DNA synthesis are also important for a retrovirus to be biologically active, and may be readily identified by one of skill in the art. For example, tRNA binds to a retroviral tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR.

The packaging signal sequence of FIV directs packaging of viral genetic material into the viral particle. A major part of the packaging signal in FIV lies between the 5' FIV LTR and the gag/pol sequence with the packaging signal likely overlapping in part with the 5' area of the gag/pol sequence.

In addition to 5' and 3' FIV LTRs, a tRNA binding site, a packaging signal, and an origin of second strand DNA synthesis, certain preferred recombinant FIV vector constructs for use herein also comprise one or more genes of interest, each of which is discussed in more detail below. In addition, the FIV vectors may, but need not, include an RNA export element (also variously referred to as RNA transport, nuclear transport or nuclear export elements) which may be the FIV RRE (Rev-responsive element) or a heterologous transport element. Representative examples of suitable heterologous RNA export elements include the Mason-Pfizer monkey virus constitutive transport element, the MPMV CTE (Bray et al., *PNAS USA* 91, 1256–1260, 1994), the Hepatitis B Virus posttranscriptional regulatory element, the HBV PRE (Huang et al., *Mol. Cell. Biol.* 13:7476–7486, 1993 and Huang et al., *J. Virology* 68:3193–3199, 1994), other lentiviral Rev-responsive elements (Daly et al., *Nature* 342:816–819, 1989 and Zapp et al., *Nature* 342:714–716, 1989) or the PRE element from the woodchuck hepatitis virus. Further RNA export elements include the element in Rous sarcoma virus (Ogert et al., *J. Virology* 70:3834–3843, 1996; Liu & Mertz, *Genes & Dev.* 9:1766–1789, 1995) and the element in the genome of simian retrovirus type 1 (Zolotukhin et al., *J. Virology* 68:7944–7952, 1994). Other potential elements include the elements in the histone gene (Kedes, *Annu. Rev. Biochem.* 48:837–870, 1970), the a interferon gene (Nagata et al., *Nature* 287:401–408, 1980), the β-adrenergic receptor gene (Koilka et al., *Nature* 329:75–79, 1987), and the c-Jun gene (Hattorie et al., *PNAS* 85:9148–9152, 1988).

FIV vector constructs which lack both gag/pol and env coding sequences may be used with the present invention. As utilized herein, the phrase "lacks gag/pol or env coding sequences" should be understood to mean that the FIV vector contains less than 20, preferably less than 15, more preferably less than 10, and most preferably less than 8 consecutive nucleotides which are found in gag/pol or env genes, and in particular, within gag/pol or env expression cassettes that are used to construct packaging cell lines for the FIV vector construct. This aspect of the invention provides for FIV vectors having a low probability of undesirable recombination with gag/pol or env sequences which may occur in a host cell or be introduced therein, for example, by transformation with an expression cassette. The production of FIV vector constructs lacking gag/pol or env sequences may be accomplished by partially eliminating the packaging signal and/or the use of a modified or heterologous packaging signal. Within other embodiments of the invention, FIV vector constructs are provided wherein a portion of the packaging signal that may extend into, or overlap with, the FIV gag/pol sequence is modified (e.g., deleted, truncated or bases exchanged). Within other aspects of the invention, FIV vector constructs are provided which include the packaging signal that may extend beyond the start of the gag/pol gene. Within certain embodiments, the packaging signal that may extend beyond the start of the gag/pol gene is modified in order to contain one, two or more stop codons within the gag/pol reading frame. Most preferably, one of the stop codons eliminates the gag/pol start site. In other embodiments, the introduced mutation may cause a frame shift in the gag/pol coding region.

Other retroviral gene delivery vehicles may likewise be utilized within the context of the present invention, including for example those described in EP 0,415,731; WO 90/07936; WO 91/0285, WO 9403622; WO 9325698; WO 9325234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and W091/02805).

Packaging cell lines suitable for use with the above described retrovector constructs may be readily prepared (see, e.g., U.S. Pat. Nos. 5,591,624 and 6,013,517, incorporated herein by reference in their entireties; and International Publication No. WO 95/30763), and utilized to create producer cell lines (also termed vector cell lines or "VCLs") for the production of recombinant vector particles. Briefly, the parent cell line from which the packaging cell line is derived can be selected from a wide variety of mammalian cell lines, including for example, human cells, monkey cells, feline cells, dog cells, mouse cells, and the like.

For example, potential packaging cell line candidates are screened by isolating the human placental alkaline phosphatase (PLAP) gene from the N2-derived retroviral vector pBAAP, and inserting the gene into the FIV vector construct. To generate infectious virus, the construct is co-transfected with a VSV-G encoding expression cassette (e.g., pMLP-G as described by Emi et al., *J. Virology* 65, 1202–1207, 1991; or pCMV-G, see U.S. Pat. No. 5,670,354) into 293T cells, and the virus harvested 48 hours after transfection. The resulting virus can be utilized to infect candidate host cells which are subsequently FACS-analyzed using antibodies specific for PLAP. Candidate host cells include, e.g., human cells such as HeLa (ATCC CCL 2.1), HT-1080 (ATCC CCL 121), 293 (ATCC CRL 1573), Jurkat (ATCC TIB 153), supT1 (NIH AIDS Research and Reference reagent program catalog #100), and CEM (ATCC CCL 119) or feline cells such as CrFK (ATCC CCL 94), G355-5 (Ellen et al., *Virology* 187:165–177, 1992), MYA-1 (Dahl et al., *J. Virology* 61:1602–1608, 1987) or 3201-B (Ellen et al., *Virology* 187:165–177, 1992). Production of p24 and reverse transcriptase can also be analyzed in the assessment of suitable packaging cell lines.

After selection of a suitable host cell for the generation of a packaging cell line, one or more expression cassettes are introduced into the cell line in order to complement or supply in trans components of the vector which have been deleted (see, e.g., U.S. Pat. Nos. 5,591,624 and 6,013,517, incorporated herein by reference in their entireties; and International Publication No. WO 95/30763). For example, packaging expression cassettes may encode either gag/pol sequences alone, gag/pol sequences and one or more of vif, rev or ORF 2, or one or more of vif, rev or ORF 2 alone and may contain an RNA export element. For example, the packaging cell line may contain only ORF 2, vif or rev alone, ORF 2 and vif, ORF 2 and rev, vif and rev or all three of ORF 2, vif and rev.

Packaging cell lines may also comprise a promoter and a sequence encoding ORF 2, vif, rev, or an envelope (e.g., VSV-G), wherein the promoter is operably linked to the sequence encoding ORF 2, vif rev, or the envelope. For packaging cell lines containing inducible gag/pol or env expression cassettes, additional expression cassettes facilitating the transactivation of the inducible promoter may be incorporated.

The expression cassette may or may not be stably integrated. The packaging cell line, upon introduction of an FIV vector, may produce particles at a concentration of greater than $10^3$, $10^4$, $10^5$, $10^6$, $10^7$, $10^8$, or, $10^9$ cfu/ml.

B. Treatment of Lysosomal Storage Diseases

In humans, there are numerous inherited metabolic diseases affecting the CNS, many of which are the result of a deficiency in a soluble lysosomal enzyme, which would benefit from FIV-based gene therapy as disclosed herein. The long-lasting expression conferred by FIV-based vectors could be improved further if coupled to recent advancements made in transcriptional regulation of transgene expression. Such vectors may find application not only to correction of lysosomal storage disease in humans, but also to diseases which may benefit from the protective effects of secreted growth factors, such as Parkinson's disease, Alzheimers disease, and the dominant neurodegenerative diseases such as Huntington's and the spinal cerebellar ataxias.

Lysosomal diseases in humans that are amenable to treatment using the methods of the invention include Batten's disease (neuronal ceroid lipofuscinosis), which has autosomal recessive inheritance (Marshman et al., Aust. N. Z. J. Ophthalmol. (1998) 26:251–254); mucolipidosis type IV, characterized by retinal degeneration and brain abnormalities (Frei et al. (1998) Neurology 51:565–569; Siegel et al. (1998) Elec. Clin. Neurophys. 106:400–403); and infantile cystinosis (Broyer, M. (1997) Rev. Prat. 47:1550–1553).

Hermansky-Pudlak syndrome, which is an often fatal autosomal recessive disorder (Feng et al. (1997) Hum. Mol. Genet. 6:793–797), is also suitable for treatment according to the invention. Feng et al. describe a mouse disease that is homologous to the human syndrome and provides an animal model for the human disease, as well as for the Chediak-Higashi syndrome. Both human syndromes are characterized by lysosomal storage defects, and HPS is a single-gene disorder. Oh et al. in Nat. Genet. 14:300–306 (1996) describe a transmembrane protein that is defective in HPS patients due to truncation caused by a frameshift mutation.

Other suitable diseases include adult form galactosialidosis (Usui et al. (1993) Metab. Pediatr. Syst. Ophthalmol. 16:19–22); Salla disease (Mancini et al. (1992) Eur. J. Pediatr. 151:590–595); Type B Niemann-Pick disease resulting from deficiency or decreased activity of sphingomyelinase (Barton et al. (1992) Metab. Pediatr. Syst. Ophthalmol. 15:16–20); multiple sulfatase deficiency, or Austin's disease (al Aqeel et al. (1992) J. Child Neurol. 7 Suppl. PS12–21); Morquio syndrome (systemic mucopolysaccharidosis IV A) which can exhibit inclusions distributed in various parts of the eye including the retinal pigment epithelium (Iwamoto et al. (1 990) Graefes Arch. Clin. Exp. Ophthalmol. 228:342–349); and β-galactosidase deficiency (Andia et al. (1978) Clin. Genet. 14:16–23).

The methods of the invention also have use in the veterinary field including treatment of domestic pets and farm animals. Mumane at al. (1994) described an ovine form of GM-1 gangliosidosis, and detected CNS abnormalities and blindness in some animals (J. Vet. Intern. Med. 8:221–223. Deficiencies of β-galactosidase and α-neuraminidase have also been reported in sheep (Murnane et al. (1989) Am. J. Pathol. 134:263–270), with CNS and ocular involvement. Stramm et al. ((1986) Invest. Ophthamol. Vis. Sci. 27:1050–1057) reported a deficiency of arylsufatase B in a recessively inherited feline lysosomal storage disease, MPS VI. Tissues affected include the retinal pigment epithelium and other regions of the eye.

C. Method for Treating and Preventing Retinal Disease, and Pharmaceutical Compositions In one aspect, the present invention provides methods which generally comprise the step of intravitreously administering a gene delivery vector which directs the expression of one or more proteins, polypeptides or enzymes to the retina in order to treat, prevent, or inhibit the progression of a retinal disease. In another aspect, the present invention provides methods for administering a gene delivery vehicle to the brain, wherein the expression of one or more polypeptides, proteins, or enzymes is directed. As utilized herein, the terms "treated, prevented, or, inhibited" refer to the alteration of a disease course or progress in a statistically significant manner. Determination of whether a disease course has been altered may be readily assessed in a variety of model systems, discussed in more detail below, which analyze the ability of a gene delivery vector to delay, prevent or rescue photoreceptors, as well as other retinal cells, from cell death, or to delay or prevent cell damage or death in the brain.

1. Retinal Diseases of the Eye

A wide variety of retinal diseases may be treated given the teachings provided herein. For example, within one embodiment of the invention gene delivery vectors are administered to a patient intravitreously in order to treat or prevent macular degeneration. Briefly, the leading cause of visual loss in the elderly is macular degeneration (MD), which has an increasingly important social and economic impact in the United States. As the size of the elderly population increases in this country, age related macular degeneration (AMD) will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with MD.

Within other embodiments, gene delivery vectors can be administered to a patient intravitreously in order to treat or prevent diabetic retinopathy, or other vascular diseases of the retina.

Within another embodiment, gene delivery vectors can be administered to a patient intravitreously in order to treat or prevent an inherited retinal degeneration. One of the most common inherited retinal degenerations is retinitis pigmentosa (RP), which results in the destruction of photoreceptor cells, and the RPE. Other inherited conditions include Sly syndrome; Bardet-Biedl syndrome (autosomal recessive);

Congenital amaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive). This group of debilitating conditions affects approximately 100,000 people in the United States alone.

Within other embodiments of the invention, gene delivery vectors can be administered to a patient intravitreously in order to treat or prevent glaucoma. Glaucoma is a heterogeneous group of disorders that share a distinct type of optic nerve damage that leads to loss of visual function. The disease is manifest as a progressive optic neuropathy that, if left untreated, leads to blindness. It is estimated that as many as 3 million Americans have glaucoma and, of these, as many as 120,000 are blind as a result. Furthermore, it is the number one cause of blindness in African-Americans. Its most prevalent form, primary open-angle glaucoma, can be insidious. This form usually begins in midlife and progresses slowly but relentlessly. If detected early, disease progression can frequently be arrested or slowed with medical and surgical treatment.

2. Lysosomal Storage Diseases of the Brain

In the brain, both neurons and cells of glial lineage are affected. The brain lysosomal storage and decreased neuronal numbers may contribute to the behavioral, memory, and cognitive deficits seem in MPS VII mice (Chang et al., Neuro Report 4:507–510, 1993). In humans, clinical features related to brain lysosomal storage include deafness and mental retardation. The morphological aspects of hearing loss in affected mice include thickening of the tympanic membrane, otitis media with expansion of the middle ear mucos, deformation of the middle ear ossicles, and inner ear alterations (Berry et al., Lab. Invest. 77:438–445, 1994).

3. Methods of Administration

Gene delivery vectors are delivered to the eye by intravitreous injection. The vitreous is approached either through the ora serata or directly through the pupil, negotiating the needle around the lens. In one application, the primary target cells to be transduced are the retinal ganglion cells, which are the retinal cells primarily affected in glaucoma. In this application, the injection volume of the gene delivery vector can large, as the volume is not constrained by the anatomy of the interphotoreceptor or subretinal space. Acceptable dosages in this instance can range from 25 $\mu$l to 1000 $\mu$l. In another application, the retinal pigment epithelium (RPE) cells are the target cells. Both cell types are targeted by the FIV virus.

Gene delivery vectors are delivered to the brain of mice by injection into the straitum or right lateral ventricle. Intraventricular injection results in transduction of both ependyma and choroidal epithelium.

4. Assays

A wide variety of assays may be utilized in order to determine appropriate dosages for administration, or to assess the ability of a gene delivery vector to treat or prevent a particular disease. Certain of these assays are discussed in more detail below.

a. Electroretinographic Analysis

Electroretinographic analysis can be utilized to assess the effect of gene delivery administration into the retina. Briefly, animals are dark adapted overnight and then in dim red light, then anesthetized with intramuscular injections of xylazine (13 mg/kg) and ketamine (87 mg/kg). Full-field scotopic ERGs are elicited with 10-$\mu$sec flashes of white light and responses were recorded using a UTAS-E 2000 Visual Electrodiagnostic System (LKC Technologies, Inc., Gaithersburg, Md.). The corneas of the rats are anesthetized with a drop of 0.5% proparacaine hydrochloride, and the pupils dilated with 1% atropine and 2.5% phenylephrine hydrochloride. Small contact lenses with gold wire loops are placed on both corneas with a drop of 2.5% methylcellulose to maintain corneal hydration. A silver wire reference electrode is placed subcutaneously between the eyes and a ground electrode is placed subcutaneously in the hind leg. Stimuli are presented at intensities of $-1.1$, 0.9 and 1.9 log cd m$^{-2}$ at 10-second, 30-second and 1-minute intervals, respectively. Responses are amplified at a gain of 4,000, filtered between 0.3 to 500 Hz and digitized at a rate of 2,000 Hz on 2 channels. Three responses are averaged at each intensity. The a-waves are measured from the baseline to the peak in the cornea-negative direction, and b-waves are measured from the cornea-negative peak to the major cornea-positive peak. For quantitative comparison of differences between the two eyes of rats, the values from all the stimulus intensities are averaged for a given animal.

b. Retinal Tissue Analysis

Retinal tissue analysis can also be utilized to assess the effect of gene delivery administration into the retina. This procedure is described in more detail below in Example 2.

c. Neurological Function

In mice, neurological function can be measured by EEG. Behavioral, memory, and cognitive function can be assayed as described. (Chang et al., Neuro Report 4:507–510, 1993.)

d. Neural Tissue Analysis

Tissues can be harvested from treated mice or primates, and processed for evaluation of lysosomal distension using routine procedures. In this invention it is useful to evaluate, for example, the ipsilateral striatum, ipsilateral cortex, and contra-lateral cortex. Measurements performed over time can indicate increasing correction of cells distant to the vector administration site. CSF can also be collected and evaluated for protein levels or enzyme activity, particularly if the vector encodes a secretable enzyme.

5. Pharmaceutical Compositions

Gene delivery vectors may be prepared as a pharmaceutical product suitable for direct administration. Within preferred embodiments, the vector should be admixed with a pharmaceutically acceptable carrier for intravitreous administration. Examples of suitable carriers are saline or phosphate buffered saline.

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Restriction and modifying enzymes, as well as other reagents for DNA manipulations were purchased from commercial sources, and used according to the manufacturers' directions. In the cloning of DNA fragments, except where noted, all DNA manipulations were done according to standard procedures. See, e.g., Sambrook et al., supra.

Figure 2:
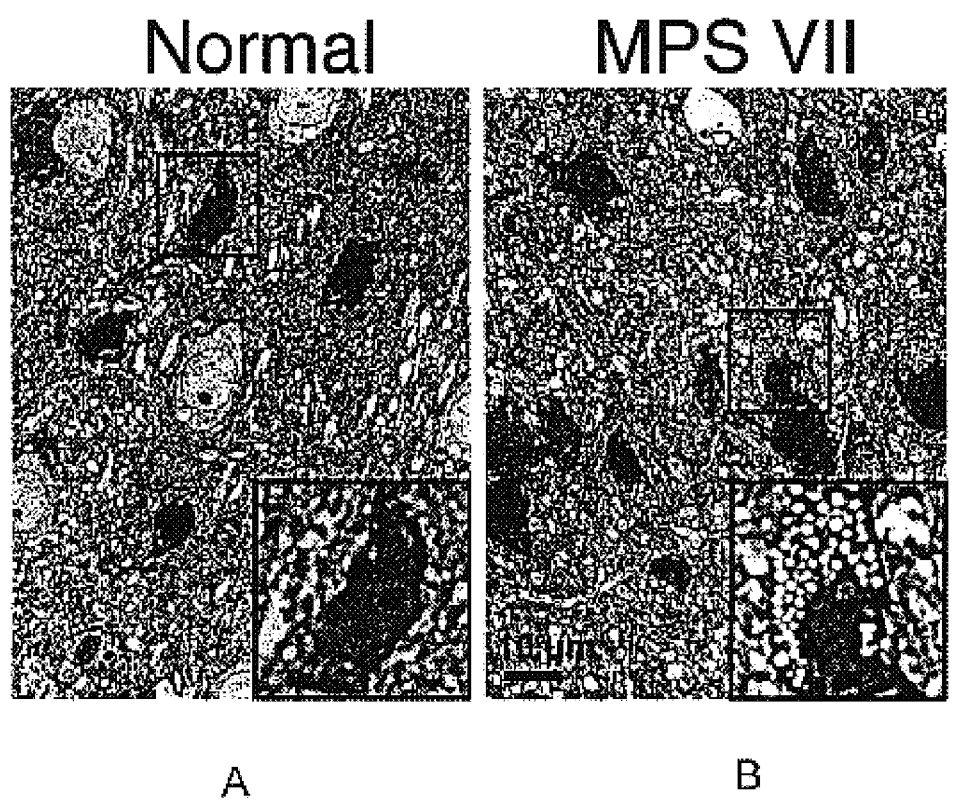

EXAMPLE 1

β-Glucuronidase Expression in Neuronal Tissue of MPS VII Mice

β-glucuronidase deficiency, or MPS VII, is representative of a group of lysosomal storage disorders in humans characterized by accumulations of proteoglycans. The disease is progressive, with most tissues affected including the CNS. Mouse models for β-glucuronidase deficiency reflect characteristics of the human disorder, and cells in diseased tissues contain numerous, distended lysosomes. In the brain, both neurons and cells of glial lineage are affected. FIG. 1 illustrates the VII mice (1B) compared to normal liver (1A). FIG. 2 illustrates lysosomal granules in brain of MPS VII mice (2B) compared to normal brain (2A).

A. FIV vectors expressing β-glucuronidase were generated which were devoid of vif and ORF 2 (FIVβglucΔvifΔorf2), as described below in Example 1B and disclosed in International Publication No. WO 99/36511, published Jul. 22, 1999. Vectors were injected into the striatum of β-glucuronidase deficient mice, and animals sacrificed 3 to 18 weeks later and tissues analyzed for transgene expression, enzyme activity, and correction of pathology.

Figure 4:
FIG. 4 shows that gene transfer with an FIV vector expressing a therapeutic gene product allows for prolonged expression of β-glucuronidase and extensive activity of β-glucuronidase throughout the brain.

FIVβgluc vector-mediated gene transfer resulted in robust levels of expression in the injected hemisphere, 3 weeks after injection of vector. A representative coronal section from a mouse sacrificed 3 weeks after injection is shown in FIG. 4. The level of activity did not decline by 18 weeks, and there was no evidence of inflammatory infiltrate.

In situ RNA analysis for human β-glucuronidase mRNA confirmed that transduction was limited to cells near the injection site, and suggests that mRNA and/or virus was not transported to distant cells. Thus, the extensive distribution of enzyme likely results from secretion by transduced cells, followed by distribution via the CSF and extracellular fluids, with uptake by distant cells.

Figure 5:
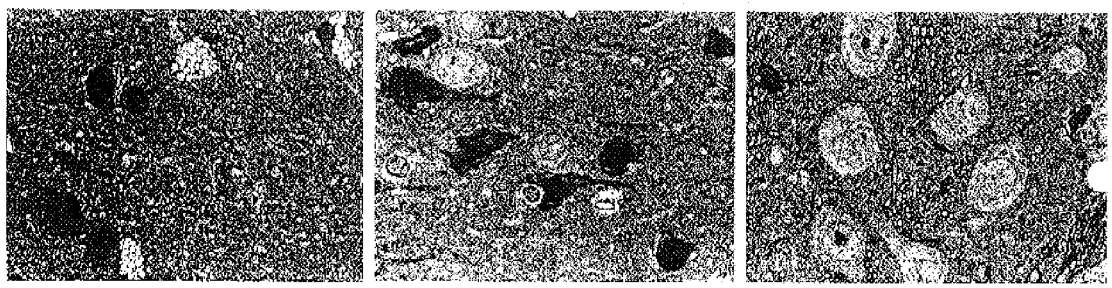
FIG. 5 shows correction of the pathologic defect in MPS VII mice when a gene is expressed from this FIV vector. There is correction in the region where the virus was injected and at remote sites. The control tissue is from a normal mouse.

Tissues harvested from β-glucuronidase deficient mice injected into the right striatum with FIVβgluc vector were also processed for evaluation of lysosomal distension. In tissues from mice sacrificed 3 weeks after gene transfer, correction was noted in the ipsilateral striatum, ipsilateral cortex, and modest reductions in storage product were noted in the contralateral cortex. By 6 weeks, there was dramatic restoration of cellular morphology in both hemispheres of the brain (FIG. 5). This extensive correction was maintained at 18 weeks the last time point studied because of the shortened life spans of these animals (approximately 6 months). The results suggest that persistent expression of this enzyme, approximately 2–5% of which is secreted, can result in correction of cells at increasing distances over time. This result indicates that focal transduction with a gene transfer vector expressing a soluble lysosomal enzyme can lead, eventually, to wide-spread dissemination of the enzyme. This is enhanced by stable expression by FIV-based vectors devoid of ORF 2 and vif.

β-glucuronidase deficient mice show progressive impairment in neurologic function as measured by EEG. In β-glucuronidase deficient mice given FIVβgluc vector, the progressive impairment is attenuated, presumably by expression of functional enzyme and clearance of storage product.

These results indicate that FIV-based vectors, devoid of accessory proteins, can globally correct a severe neurologic deficit in the brains of mice suffering from lysosomal storage disease.

B. The effects of FIVβglucΔvifΔorf2 gene transfer on learning and memory was also evaluated after injection into 15 wk old β-glucuronidase-deficient mice with established cellular deficits. FIV vectors for use in this example were generated essentially as described in International Publication No. WO 99/36511, published Jul. 22, 1999. Specifically, FIV packaging constructs were generated in a series of steps from the full-length FIV molecular clone, FIV-34TF10 (NIH AIDS Research and Reference Reagent Program, Cat. No. 1236; Phillips et al., *J. Virol.* 66: 5464, 1992, Talbott et al., *PNAS* 86: 5743, 1989) as described (Johnston et al., *J Virol* 73:4991–5000, 1999). The FIV vector construct, pVET$_L$Cβgal (pVET$_L$Cβ in ref (Johnston et al., *J Virol* 73:4991–5000, 1999), was generated by inserting an expression cassette consisting of the CMV promoter followed by the β-galactosidase gene into the pVET$_L$ FIV vector backbone. The pVET$_L$ backbone contains the FIV 5' LTR, in which the FIV U3 region is replaced by the CMV promoter/enhancer, 0.5 kb of Gag coding region, a multicloning site and the FIV 3' LTR (Johnston et al., *J Virol* 73:4991–5000, 1999). To construct pVET$_L$Rβgluc, an RSV promoter lacking a functional polyadenylation signal was first liberated from pUC19RSV by digestion with BamH I and Sal I. The resulting fragment was inserted into similarly digested pVET$_L$ to generate pVET$_L$RSV. Next, the β-glucuronidase cDNA was liberated from pAdRSV4 by digestion with Xho I and the resulting fragment ligated into Sal I digested/CIP treated pVET$_L$RSV to generate pVET$_L$Rgluc (+polyA). A portion of the β-glucuronidase cDNA was amplified by PCR and the product digested with Bgl II and Xho I in order to remove the polyadenylation signal from the cDNA. To generate pVET$_L$Rgluc, the resulting fragment was joined in a three-way ligation with an Nco I/Bgl II fragment and a Xho I/Nco I fragment from pVET$_L$Rgluc (+polyA). All constructs were screened by restriction enzyme digestion and the sequence of regions amplified by PCR confirmed by sequence analysis. Oligonucleotides were synthesized by Operon Technologies, Inc.(Alameda, Calif.) and sequences as well as more detailed cloning methods are available upon request. Construction of the VSV-G envelope expression plasmid, pCMV-G, has been described (Yee et. al., *PNAS* 91:9564, 1994). Pseudotyped FIVβgluc and FIVβgal vector particles were generated by transient transfection of plasmid DNA into 293T cells plated one day prior to transfection at a density of 2.8×10$^6$ cells per 10 cm diameter culture dish. Cotransfections were performed using a 1:2:1 molar ratio of FIV packaging construct, FIV vector construct and VSV-G envelope-expressing plasmid. DNA complexes were prepared using calcium phosphate (Profectin kit; Promega Corp. Madison, Wis.) and transfected into cells according to the manufacturer's instructions. The medium was replaced 8–16 hr after transfection and the supernatant harvested twice between 32 and 48 hr after the start of transfection. The harvested supernatants were filtered through a 0.45 M Nalgene filter and stored at −70° C. or concentrated prior to storage. Supernatants were concentrated by centrifugation (Johnston et al., *J Virol* 73:4991–5000). Vector titers were determined on HT1080 cells by serial dilution and assay for β-galactosidase or β-glucuronidase expression (Li et al., *PNAS* 92:7700–7704, 1995).

C57BL/6 mice were obtained from Harlan Sprague (Indianapolis, Ind.). These mice are deficient in β-glucuronidase and provide an accepted animal model for the study of lysosomal storage disease. Mice with a deficiency in this soluble lysosomal enzyme manifest both visceral and CNS manifestations, thus recapitulating the human syndrome, also known as Sly syndrome or MPS VII. The inability to appropriately degrade proteoglycans leads to progressive accumulation of precursor products in the lysosomes. In this storage disease enzyme production and release by a subpopulation of parenchymal cells within the brain results in widespread clearing of metabolic precursors. For virus injections, the β-glucuronidase-deficient mice were anesthetized with ketamine/xylazine (ketamine 100–125 mg/kg, xylazine 10–12.5 mg/Kg). The bregma was then exposed by incision and used as a zero coordinate and injections made stereotactically into the striatum or ventricle as previously described (Ghodri et al., *Hum Gene Ther* 9:2331–2340, 1998).

For histological studies the mice were injected unilaterally with 5 µl (intraparenchymal) or 10 µl (intraventricular) of FIVβgal, FIVβgalΔvif, FIVβgalΔorf2, or FIVβgalΔvifΔorf2 or FIVβglucΔvifΔorf2. Animals were sacrificed at 3, 6, 9, 15, and 18 weeks after gene transfer and brains analyzed for enzyme activity, volume analysis, in-situ RNA hybridization, and analysis of storage vacuoles as previously described (Li et al., *PNAS* 92:7700–7704, 1995).

Delivery of FIVβglucΔvifΔorf2 to the brains of eight-week old β-glucuronidase deficient mice resulted in transduction of cells near the injection site. However, the level of enzyme activity measured by the histological assay extended well beyond the focus of transduced cells, with 20–25% of the hemisphere positive for enzyme activity, and was relatively stable. Tissues harvested from β-glucuronidase-deficient mice injected into one hemisphere of the brain with FIVβglucΔvifΔorf2 were examined for the effects of gene therapy on lysosomal distension. In tissues from mice sacrificed 3 weeks after gene transfer, histological correction was observed in the ipsilateral striatum, ipsilateral cortex, and modest reductions in storage product seen in the contralateral cortex. No inflammation was found in brains of animals sacrificed at this time. By 6 weeks, there was dramatic restoration of cellular morphology in both hemispheres of the brain indicative of cross-correction. The absence of lysosomal inclusions was maintained through the course of the study (18 weeks) suggesting that persistent expression of this enzyme from transduced cells, approximately 2–5% of which may be secreted, results in correction of cells at increasing distances over time.

These findings have direct therapeutic implications because they show that focal transduction with lentivirus-based vectors expressing a soluble lysosomal enzyme can lead to wide-spread dissemination of the gene product.

Gene therapy-mediated correction of the histopathological defects in the CNS of animals with established, advanced, neurodegenerative disease has not been shown to result in improved neurological function. Such an improvement after gene therapy would indicate that the CNS disease might in part be reversible. Accordingly, the ability of FIVβglucΔvifΔorf2 to restore or improve CNS function was evaluated. Specifically, the affect of FIV-mediated gene transfer of FIVβglucΔvifΔorf2 on spatial learning ability was examined. The repeated acquisition and performance chamber (RAPC) was utilized to assess spatial learning and memory in both gus +/− and gus −/− mice (Brooks et al., Repeated Acquisition and Performance Chamber for Mice: A Paradigm for Assessment of Spatial Learning and Memory. Neurobiology of Learning & Memory, (In Press)). In brief, mice were first deprived of water for 12–16 hours and habituated to a saccharin solution before being introduced into the RAPC for the first time. A 0.2% solution of saccharin dissolved in water was provided for 30 minutes twice a day for 2 days, after which regular drinking water was provided ad libitum. Subsequently, all mice were given four apparatus habituation sessions, each allowed to freely explore the chambers and consume saccharin drops: 1) Placed in front and in back of all doors with all doors taped open (session A); 2) in front and in back of all doors with all doors unlatched (session B); 3) only in back of C and D doors with all doors unlatched (session C); 4) only in back of D doors with all doors unlatched (session D).

Following habituation, mice were tested over the course of four experimental sessions (sessions 1/2 and 3/4 were separated by 5 weeks). A 12 hour water deprivation period preceded all behavioral test sessions, which occurred approximately every third day, with ad libitum water on non-test days for the remainder of the study. Each session consisted of three presentations each of the repeated acquisition (RA) component and the performance (P) component. In the RA component, the specific door sequence changed unpredictably with each successive test session (not trial) according to a matrix that prevented the same door on a given panel from being open on consecutive sessions. During the P component, the sequence of doors leading to saccharin was constant across sessions. A static audio signal was played for the duration of the P component as a discriminative stimulus signaling that component, whereas the absence of the audio signal served as the discriminative stimulus for the RA component. A total of three trials (from goal box to saccharin) were carried out during each presentation of the RA and P components during a session, for a total of 18 trials per session. Latency was measured as the time required for a subject to leave the start box, successfully navigate through the four compartments, and consume the saccharin solution in the goal box. Mice were manually placed in the goal box in the event of failure to reach it within 10 minutes on any trial. In addition to latency, the number and sequence of door errors made by the subject were also recorded.

Initial RAPC experiments were performed on untreated β-glucuronidase-deficient and age-matched, heterozygous, control animals to define baseline learning and performance abilities. At 8 weeks of age comparison of the number of errors made by the β-glucuronidase deficient and control mice indicated that the β-glucuronidase deficient mice have a baseline impairment in learning. Baseline differences (pre-treatment) in numbers of errors and latencies in the RAPC were evaluated using repeated measures analyses of variance with component (learning and performance) and session (1–4) as within group factors and β-glucuronidase status (+/− vs −/−) as a between-group factor. These were followed, where appropriate by one factor ANOVAs (β-glucuronidase status) for individual session data. Statistical assessment of changes in these measures post-treatment were carried out separately for each treatment (FIVβgal and FIVβgluc) and for each component (learning and performance) in RMANOVAs with β-glucuronidase status (+/− vs −/−) as a between-group factor and session (10–14) as within group factors. Subsequent one factor ANOVAs were used where appropriate for determining differences between +/− vs −/− groups for each session. Fourteen days following gene transfer animals were re-assessed in the RAPC as described above. Three sessions were conducted post-operatively (each session separated by one week) to assess the effects of FIV mediated gene transfer.

Baseline Differences between +/− vs. −/− Groups: β-glucuronidase deficient mice (−/−) showed significantly greater numbers of errors in the RAPC in both the learning and the performance component of the session over the 4 baseline sessions in which they were tested (main effect of group: $F(1,12)=742.05$, $p=0.0001$) with subsequent post-hoc assessments confirming differences between the two groups during each session and in both the learning and performance components (all p values<0.05). Mean group error values of the +/− group in the learning component ranged from 32 to 47 whereas corresponding values for the −/− mice were 66 to 88. Similarly, numbers of errors in the performance component of the +/− group ranged from 10 to 16 with values of the −/− group higher at 24 to 29. Latencies and error number in the RAPC learning component increased in β-glucuronidase deficient mice tested between the 8 th and 13 th week of age indicating progressive impairment of cognitive function.

Latency values between the +/− and −/− groups: Latency values also differed between the +/− and −/− groups (main effect of group: $F(1,12)=6.17$, $p=0.029$). In the learning component, −/− mice actually exhibited significantly shorter latencies during the first session, but these subsequently increased, such that by sessions 3 and 4, latencies of the −/− group were significantly higher than those of the +/− group (approximately 165 vs. 120 sec.). Similarly, latency values of the −/− group were also significantly shorter during the first 2 sessions in the performance component of the schedule (approximately 25 vs. 50 sec.) but rose over the subsequent time period such that by session 4 their latency values significantly exceeded those of the +/− group (51 vs. 59 sec) and this represented almost a doubling of latencies across time for the −/− group.

Post-Treatment Differences: Mice from the −/− group that received FIVβgal continued to show significantly greater numbers of errors in both the learning and the performance components relative to +/− mice correspondingly treated ($F(1,3)=386.4$, $p=0.0003$ and $F(1,3)=262.98$, $p=0.0005$) for the learning and performance components, respectively). The magnitude of the differences remained comparable to those seen prior to treatment. Similarly, −/− mice that received FIVβgal also continued to sustain longer latencies than did +/− mice ($F(1,3)=107.5$, $p=0.0019$ and $F(1,3)=12.96$, $p=0.037$, respectively, for the learning and performance components). These differences were sustained across sessions as indicated by the absence of any significant interaction of group by sessions in these analyses.

In contrast, mice from the −/− group that received FIVβgluc no longer evidenced any differences from the +/− mice that received FIVβgluc in the number of errors in the learning component (main effect of group, both p values>0.05). Numbers of errors for the −/− and +/− groups averaged approximately 36 and 39, respectively in the learning component. Correspondingly, the numbers of errors of −/− mice that received FIVβgluc were initially higher than those of the +/− mice that received FIVβgluc, but they declined across the course of sessions (interaction of group by session=$F(1,6)=28.3$, $p=0.0009$) such that by the final session, values no longer differed ($p=0.18$). Similarly, latency differences that were observed between the +/− and −/− groups prior to treatment were no longer evident following FIVβgluc in either the learning ($p=0.18$) or the performance component ($p=0.32$) of the schedule.

RAPC tests done 2 and 3 weeks after gene transfer demonstrated marked differences between the experimental groups. The data from the RAPC tests acquired after gene transfer indicated a significant improvement in the learning component in β-glucuronidase deficient mice that received FIVβglucΔvifΔorf2. Interestingly, there was no statistical difference between β-glucuronidase deficient mice injected with FIVβglucΔvifΔorf2 and FIVβgalΔvifΔorf2-injected control mice. Because there was no decline between the FIVβgalΔvifΔorf2 heterozygous control mice from their pre-injections values, the βgal gene transfer itself did not reduce the performance or learning components of the control group. Thus, FIVβglucΔvifΔorf2 gene transfer had a profound positive impact on the progressive neurodegenerative disease in the β-glucuronidase deficient mouse model. The RAPC data indicate that gene transfer restored cognitive function to brains of β-glucuronidase deficient mice.

The combined results are important because they show that FIV-based vectors, devoid of accessory proteins, can reverse a severe neurologic deficit in the brains of mice with an established lysosomal storage disease.

EXAMPLE 2

Transgenic Rat S334ter as a Model for Photoreceptor Degeneration

This example describes the S334ter transgenic rat as a model for photoreceptor degeneration. Briefly, rhodopsin is a seven-transmembrane protein found in photoreceptor outer segments, which acts as a photopigment. The S334 ter mutation results in the truncation of the C-terminal 15 amino acid residues of rhodopsin and is similar to rhodopsin mutations found in a subset of patients with retinitis pigmentosa (RP). RP is a heterogeneous group of inherited retinal disorders in which individuals experience varying rates of vision loss due to photoreceptor degeneration. In many RP patients, photoreceptor cell death progresses to blindness. Transgenic S334ter rats are born with normal number of photoreceptors. The mutant rhodopsin gene begins expression at postnatal day 5 in the rat, and photoreceptor cell death begins at postnatal day 10–15. In transgenic line S334ter-3, approximately 70% of the outer nuclear layer has degenerated by day 60 in the absence of any therapeutic intervention. The retinal degeneration in this model is consistent from animal to animal and follows a predictable and reproducible rate. This provides an assay for therapeutic effect by morphological examination of the thickness of the photoreceptor nuclear layer and comparison of the treated eye to the untreated (contralateral) eye in the same individual animal.

A. Retinal Tissue Analysis

The rats are euthanized by overdose of carbon dioxide inhalation and immediately perfused intracardially with a mixture of mixed aldehydes (2% formaldehyde and 2.5% glutaraldehyde). Eyes are removed and embedded in epoxy resin, and 1 $\mu$m thick histological sections are made along the vertical meridian. Tissue sections are aligned so that the ROS and Muller cell processes crossing the inner plexiform layer are continuous throughout the plane of section to assure that the sections are not oblique, and the thickness of the ONL and lengths of RIS and ROS are measured. These retinal thickness measurements are plotted and establish the baseline retinal degeneration rates for the animal model. The assessment of retinal thickness is as follows: briefly, 54 measurements of each layer or structure are made at set points around the entire retinal section. These data are either averaged to provide a single value for the retina, or plotted as a distribution of thickness or length across the retina.

For FIV vector evaluation experiments in vivo, a suitable line of transgenic rats is TgN(s334ter) line 4 (abbreviated s334ter 4). Expression of the mutated opsin transgene begins at postnatal day P5 in these rats, leading to a gradual death of photoreceptor cells. These rats develop an anatomically normal retina up to P15, with the exception of a slightly increased number of pyknotic photoreceptor nuclei in the outer nuclear layer (ONL) than in non-transgenic control rats. In this animal model, the rate of photoreceptor cell death is approximately linear until P60, resulting in loss of 40–60% of the photoreceptors. After P60, the rate of cell loss decreases, until by one year the retinas have less than a single row of photoreceptor nuclei remaining.

EXAMPLE 3

β-Glucuronidase or β-Galactosidase Expression After FIV-Mediated Gene Transfer in Retinal Pigment Epithelium of Glucuronidase-deficient Mice A. In this example, the cellular targets for transduction following intravitreal (corneal and ora serata) injection of FIVβgal (feline immunodeficiency virus expressing *E. coli* β-galactosidase) were tested. One microliter was injected intravitreally. Results show that both corneal endothelium and cells of the iris could be transduced. Intravitreal injection of FIBβgal also resulted in very efficient transduction of the RPE.

Figure 3:
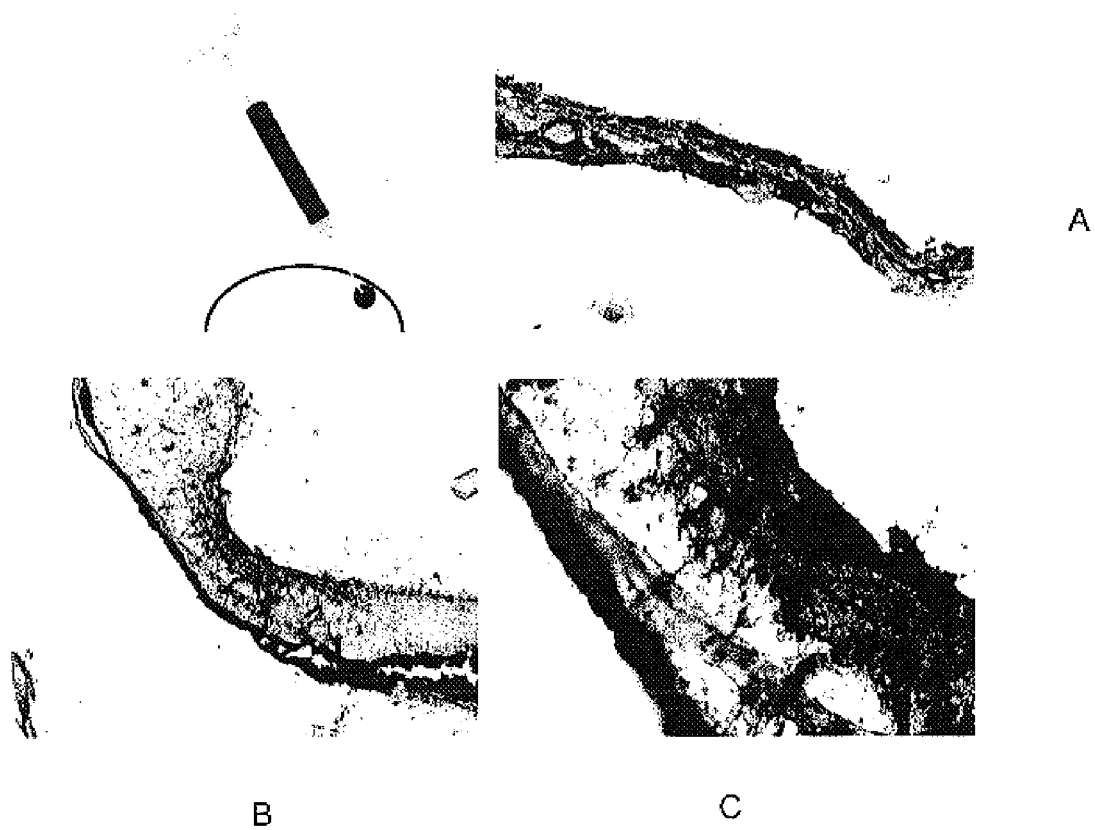
FIGS. 3A–3C show the result of gene transfer to the eye after intravitreous injection of FIVβgal with evidence of gene transfer to the iris (3A) and retina (3B and 3C, a higher power view).

Immunohistochemistry following intravitreal injection of a mixture of confirmed AdGFP (adenovirus expressing green fluorescent protein) and FIVβgal confirmed that both viruses could mediate transduction of corneal endothelium and cells of the iris (FIG. 3A), and that FIV could also transduce cells in the retina (FIGS. 3B and 3C). In some cases, photoreceptor cells were also transduced following intravitreal injection of FIVβgal. Transgene expression with FIVβgal remained relatively stable for 21 days, the last time point tested. The efficacy of intravitreal injection of FIVβgluc (FIV expressing β-glucuronidase) was tested using an animal model of RPE-dependent photoreceptor cell degeneration, the β-glucuronidase deficient mouse. Intravitreal injection of FIVβgluc to the eyes of β-glucuronidase deficient mice resulted in rapid reduction (within 2 weeks) of the lysosomal storage defect within the RPE.

Vector is administered to the vitreous as described in Li, T. And Davidson, B. L. (1995) *Proc. Natl. Acad. Sci.* 92:7700–7704. β-glucuronidase expression is measured as described by Li and Davidson (1995).

B. β-glucuronidase-deficient and Balb/C mice were used to assess the ability of FIV vector particles to transfer genes intravitreally. Balb/C mice were used for β-gal and eGFP injections due to the lack of pigmentation in the eye, therefore allowing the transgene product to be visualized easier. FIV packaging constructs were generated in several steps from the full-length FIV molecular clone, FIV-34TF10 (NIH AIDS Research and Reference Reagent Program, Cat. No. 1236; Phillips et al., *J. Virol.* 66: 5464, 1992, Talbott et al., *PNAS* 86: 5743, 1989) as described above in Example 1B. In particular, the FIV vector constructs were generated by insertion of an expression cassette into the pVET$_L$ FIV vector backbone (Johnston et al., *J Virol* 73:4991–5000, 1999). β-galactosidase expression was driven by the CMV promoter, while the β-glucuronidase expression was driven by the RSV promoter (Johnston et al., *J Virol* 73:4991–5000, 1999). The construction of VSV-g envelope expression plasmid, pCMV-G, has been previously described (Yee et al., *PNAS* 91:9564–9568, 1994). The generation of psuedotyped FIVβgal and FIVβgluc vector particles through transient transfection has been described (Johnston et al., *J Virol* 73:4991–5000, 1999).

All animals used in this example were between 4 and 8 weeks old and weighed between 12 and 24 grams. Mice were anesthetized with Ketamine-Xylazine (ketamine, 100–125 mg/kg; xylazine, 10–12.5 mg/kg). Eyes were dilated with 0.2% cyclopentolate, 0.5% phenylephrine, and 0.05% tropicamide. After dilation a drop of 0.5% proparacaine was administered as a topical anesthetic. A microscalpel was used to make a small self closing incision in the cornea just central to the free border of the iris. A 5 microliter Hamilton syringe with a fixed 1 inch blunt 33 gauge needle (Reno, Nev.) was inserted through the incision in the cornea and slid between the iris and the lens into the posterior chamber of the eye where 1–2 microliters of virus (FIV, $1 \times 10^8$ TU, Ad $1 \times 10^{10}$ IU) or saline was injected into the vitreous. Injections were observed at low magnification with a stereo microscope. The incision was coated with antibiotic ointment to help prevent leakage and infection. To aid recovery, the animals were injected with 1 milliliter normal saline subcutaneously and placed under a heat lamp.

Animals sacrificed for histochemical analysis were anesthetized and perfused with 2% paraformaldehyde in PBS. Eyes were enucleated and postfixed for 4 hours in 2% paraformaldehyde, after postfixation the lens was removed and the eyes were cryoprotected in 30% sucrose in PBS. The eyes were frozen in O.C.T. (Sakura Finetek U.S.A., Torrence, Calif.) and 10-μm slide sections were prepared.

For β-galactosidase staining, slides were rinsed with PBS and then reacted with 35 mM $K_3Fe(CN)_6$, 35 mM $K_4Fe(CN)_6$, 2 mM $MgCl_2$, and 5-bromo-4-chloro-3-indoyl-β-D-galactopyranoside (X-Gal, 1 mg/ml; Sigma, St. Louis, Mo.) in PBS for 4 hours at 37° C. to identify β-galactosidase activity.

To visualize β-glucuronidase activity, slides were fixed with an acetone-formalin solution, washed two times for 5 minutes with 0.05 M sodium acetate buffer, pH 4.5, and incubated in 0.25 mM Naph-As-Bi-β-glucuronidide (Sigma, St. Louis, Mo.) in 0.05 M sodium acetate buffer, pH 4.5, all at 4° C. The slides were then developed for 2 hours at 37° C. with 0.25 mM Naph-As-Bi-β-glucuronidide in 0.05 M sodium acetate buffer, pH 5.2, with 1:500 2% hexazotized pararosaliline (Sigma) (Bancroft, 1982; Roessler, 1994). Slides were subsequently dried and coverslipped with permount (Fisher).

For co-infection experiments, equal volumes of FIVβgal and AdeGFP (FIV, $1 \times 10^8$ TU, Ad $1 \times 10^{10}$ IU) were mixed and 2 μl injected intravitreally. To visualize both transgenes simultaneously, we stained immunohistochemically with a rabbit polyclonal antibody for β-galactosidase (Sigma, St. Louis, Mo.) followed by a rhodamine secondary antibody (Jackson). The rabbit polyclonal antibody was preabsorbed for 24 hours on naive mouse tissue. All antibodies were diluted in 3.0% BSA crystilline fraction (Sigma, St. Louis, Mo.) and 0.3% saponin (Sigma, St. Louis, Mo.) in PBS. Fluorescence was observed with a Leica DMRBE and digital images captured with a spot rt camera.

Animals for morphological analysis were sacrificed at 2, 7, or 12 weeks post-injection. Animals were anesthetized and perfused with 2% paraformaldehyde, 2.5% gluteraldehyde in PBS. Eyes were enucleated and postfixed in the same fixative for 4 hours. The lenses were removed and the eyes were further postfixed in 1% $OsO_4$ in PBS. After fixation, eyes were dehydrated and embedded in SPURRS resin (EMS). Blocks were sectioned with a diamond knife (EMS) at 90 nm and mounted on copper grids. The sections were stained with lead citrate and uranel acetate and viewed on a Hitachi 7000 transmission electron microscope.

As explained above, Balb/C mice were used for β-gal and eGFP injections due to the lack of pigmentation in the eye, therefore allowing the transgene product to be visualized easier. Eyes were evaluated at either 1 or 3 weeks after FIVβgal injection. β-galactosidase-positive cells were found predominantly in the retinal pigmented epithelium (RPE). Positive cells were also seen in the ciliary process, iris, and corneal endothelium. The distribution of positive cells did not vary over time.

These results were dissimilar to previously published adenoviral intravitreal injection data. An intravitreal injection of recombinant adenovirus results in mainly corneal endothelium and iris cells positive for the transgene and no positive cells in the RPE, this result is similar to the results published by Li et al., *Invest Opthalmol Vis Sci* 35:2543–2549, 1994. To test whether the positive cells in the RPE were due to the FIV vector or the injection technique a mixing experiment was performed. Equal volumes of Ad5RSVeGFP and FIVβgal were mixed and injected 2.0 μl in the vitreous. GFP and β-gal positive cells were both present in the anterior chamber of the eye, but only β-gal positive cells were found in the RPE. Interestingly, there was an increase in the number of β-gal positive cells found in the corneal endothelium when the FIV was injected in concert with the AV.

Treated MPS mouse eyes were examined for β-glucuronidase activity by histochemical stain as described above. The red precipitate reaction product may be obscured by the pigmentation in areas of the eye. Due to the secreted nature of β-glucuronidase positive staining cells were found throughout the eye at all time points (2, 7, and 12 weeks). These eyes were analyzed for the presence of distended lysosomes using electron microscopy. The three main cell types that were evaluated for distended lysosomal presence were the corneal endotbelium, nonpigmented epithelium of the ciliary process, and the retinal pigmented epithelium. Buffer injected and non-treated eyes showed numerous large distended lysosomes within the cytoplasmic space in all of these cell types as well as other cell types throughout the eye. In the cases of the three aforementioned cell types, all appeared swollen and larger than the cells in age-matched control animals. In the case of the RPE the pigment granules were displaced to the apical surface. However, the neural retina remained relatively unaffected with very few cells containing notable distended lysosomes.

At two weeks post-injections of FIVβgluc, the pathological differences were striking under low magnification electron microscopy (2,000×). The distended lysosomes had near completely disappeared in all three cell types evaluated. The phenotypic correction was most dramatic in the RPE and nonpigmented epithelium of the ciliary process as the cells of the treated animals were almost indistinguishable from those of the control normal animals. The correction of the corneal endothelium was also quite dramatic but not as complete as found in the other cell types. There were still some small distended lysosomes found in some of the cells. These results held true for all time points tested with one surprise addition at the 12 week time point. In addition to the corneal endothelium being partially phenotypically corrected, the distended lysosomes within the keratocytes of the corneal stroma were also significantly reduced.

In addition to looking for phenotypical correction of the lysosomal distention in the eye, β-glucuronidase enzyme levels were measured in different ocular tissues. At the time of sacrifice the fluid was removed from the eye and the cornea and retina were dissected out for analysis.

These results show that after an intravitreal injection of recombinant FIV encoding for the β-glucuronidase gene, there was significant amelioration of the distended lysosomal phenotype in several of the affected eye tissues. Surprisingly, in addition to the expected correction of the phenotype in the RPE and corneal endothelium as shown with adenoviral gene therapy to the MPS VII mouse eye (Li and Davidson, *PNAS* 92:7700–7704, 1995) correction was observed in the non-pigmented epithelium of the ciliary process and the keratocytes of the corneal stroma. Correction of the phenotype was not limited to the cells that were infected with the virus as shown by FIVβgal injections. Corneal endothelial cells and the non-pigmented epithelium of the ciliary process were sporadically infected and no positive keratocytes were found. Therefore correction of the phenotype in these cells is most likely attributable to the uptake of extracellular β-glucuronidase that has been secreted by transduced cells.

EXAMPLE 4

FIV-Mediated Gene Transfer to the CNS and Liver of β-Glucuronidase Deficient Mice An FIV vector encoding the gene for β-glucuronidase (FIVβgluc) was injected into the CNS (Striatum) and systemic circulation of β-glucuronidase deficient mice. The distribution of enzyme activity and the extent of pathological correction were assessed. β-Glucuronidase activity was extensive in the ipsilateral stratum 21 days post intraparenchymal injection of FIVβgluc to the CNS. Activity was also robust in the ipsilateral frontal and parietal cortex, the ependymal cells lining the ventricles, and the corpus callosum. In the contralateral hemisphere enzyme activity was noted but to a lesser degree. Animals sacrificed at 42, 84, and 126 days following gene transfer continued to exhibit sustained levels of enzyme activity in the same regions. Semithin sections from the striatum and cortex of β-glucuronidase deficient animals were analyzed for lysomal accumulation. There was a marked reduction in the number of distended vacuoles in both neurons and glial cells bilaterally, indicating correction of pathology.

Twenty-one days after intravenous administration of FIVβgluc into the tail veins of deficient mice, histological sections showed β-glucuronidase activity localized to both hepatocytes and Kupffer cells in the liver. Quantitative measurements using a fluorometric assay detected β-glucuronidase activity corresponding to 2% of wild-type activity. Analysis of semi-thin section of liver showed this amount of activity to be partially corrective, significantly reducing lysosomal distention in hepatocytes. These data indicate that FIV-mediated gene therapy is effective in an in vivo model for transduction of all cell types in the CNS and liver. Furthermore, reversal of the pathology can be achieved and maintained in both organ systems.

Accordingly, lentiviral vectors and methods of using the same for the treatment of brain and eye lysosomal storage disorders have been disclosed. From the foregoing, it will be appreciated that, although specific embodiments of the invention have been described herein for purposes of illustration, various modifications may be made without deviating from the spirit and scope of the appended claims.

What is claimed is:

1. An FIV vector, comprising a 5' FIV LTR, a tRNA binding site, a packaging signal, a promoter operably linked to a polynucleotide encoding a protein selected from the group consisting of β-glucuronidase, neuraminidase, sphingomyelinase, sulfatase, arylsulfatase β, α-neuraminidase, gangliosidase, tripeptidyl protease, CLN3, and palmitoyl protein thioesterase (PPT), an origin of second strand DNA synthesis and a 3' FIV LTR, wherein the FIV vector is devoid of vif and ORF 2.

2. The FIV vector of claim 1, wherein the protein is β-glucuronidase.

3. An FIV vector particle comprising the FIV vector of claim 1.

4. A host cell transduced with the FIV vector particle of claim 3.

5. An FIV vector comprising a 5' FIV LTR, a tRNA binding site, a packaging signal, a polynucleotide encoding β-glucuronidase operably linked to an FIV LTR promoter or a promoter element, an origin of second strand DNA synthesis and a 3' FIV LTR, wherein the FIV vector is devoid of vif and ORF 2.

6. The FIV vector of claim 5, wherein the promoter element is a CMV, RSV or SV40 promoter.

7. An FIV vector particle comprising the FIV vector of claim 5.

8. A host cell transduced with the FIV vector particle of claim 7.

9. A method of treating a glucuronidase-related lysosomal storage disorder of the eye or brain comprising providing the FIV vector particle of claim 7 to a vertebrate subject, wherein the FIV vector particle is administered to the subject in vivo, intravitreally, intraventricularly or via the striatum under conditions whereby the protein encoded by the polynucleotide is expressed in a cell of the vertebrate subject and secreted at a level sufficient to treat the lysosomal storage disorder.

10. The method of claim 9, wherein said lysosomal storage disorder is a disorder of the eye and is selected from the group consisting of macular degeneration, diabetic retinopathy, and inherited retinal degeneration.

11. The method of claim 9, wherein the lysosomal storage disorder is of the eye and the FIV vector particle is administered intravitreally.

12. The method of claim 9, wherein the lysosomal storage disorder is of the brain and the FIV vector particle is administered intraventricularly.

13. The method of claim 9, wherein the lysosomal storage disorder is of the brain and the FIV vector particle is administered via the striatum.

* * * * *